United States Patent [19]
Hirota et al.

[11] Patent Number: 5,920,007
[45] Date of Patent: Jul. 6, 1999

[54] PARTICLE SENSOR THAT DISTINGUISHES BETWEEN PARTICLES AND BUBBLES IN A FLUID

[75] Inventors: Toshikazu Hirota, Kuwana; Kazuyoshi Shibata, Nagoya; Yasuhito Yajima, Haguri-gun, all of Japan

[73] Assignee: NGK Insulators, Ltd., Japan

[21] Appl. No.: 08/855,395

[22] Filed: May 13, 1997

[30] Foreign Application Priority Data

May 16, 1996 [JP] Japan .................................. 8-121460
Dec. 3, 1996 [JP] Japan .................................. 8-322661

[51] Int. Cl.$^6$ ........................... G01N 15/06; G01N 29/02
[52] U.S. Cl. .......................... 73/61.75; 310/338
[58] Field of Search ................. 73/61.75, 61.71, 73/865.5; 340/627, 631; 310/338

[56] References Cited

U.S. PATENT DOCUMENTS

| | | |
|---|---|---|
| 3,816,773 | 6/1974 | Baldwin et al. .................. 310/319 |
| 3,841,144 | 10/1974 | Baldwin . |
| 3,854,323 | 12/1974 | Hearn et al. ........................ 73/61.75 |
| 4,131,815 | 12/1978 | Boatright . |
| 4,149,415 | 4/1979 | Harbour . |
| 4,240,287 | 12/1980 | Mast et al. ........................ 73/61.75 |
| 5,698,931 | 12/1997 | Shibata et al. ..................... 310/338 |

FOREIGN PATENT DOCUMENTS

0675355  10/1995  European Pat. Off. .

*Primary Examiner*—Michael Brock
*Attorney, Agent, or Firm*—Parkhurst & Wendel, L.L.P.

[57] ABSTRACT

A particle sensor includes a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals. The sensor has a means capable of selectively detecting any vibration of the vibrating section having a frequency higher than the primary resonance frequency of the sensor element. This particle sensor has improved sensitivity to solid particles and can distinguish the signals generated by collision of solid particles, from the signals generated by collision of bubbles, at a high accuracy.

9 Claims, 12 Drawing Sheets

PARTICLE SENSOR THAT DISTINGUISHES BETWEEN PARTICLES AND BUBBLES IN A FLUID

BACKGROUND OF THE INVENTION

1. Field of the Invention

The present invention relates to a particle sensor for detecting the solid particles contained in a fluid.

2. Description of Related Art

When solid particles are present in a fluid (a liquid or a gas), it is necessary in some cases to detect the presence of the solid particles. Detection of such solid particles is particularly important when the solid particles present in the fluid badly affect the intended action of the fluid.

Lubricating oils (e.g. engine oils) are used in internal combustion engines of automobiles or heavy machinery in order to reduce the frictional resistance and abrasion of the rotating surfaces and sliding surfaces of the engines. Operation of such internal combustion engines generates solid particles (e.g. metal fine particles) caused by abrasion, and the solid particles are taken into the lubricating oils and accelerate, in some cases, the abrasion of the rotating surfaces and sliding surfaces. The solid particles, etc. present in the lubricating oils are ordinarily removed by the use of a filter such as oil filter or the like. The condition of the lubricating oils can be monitored in detail by detecting the solid particles present in the lubricating oils.

Hydraulic oils and flushing oils are used in power transmission mechanisms (e.g. transmission), oil hydraulic pipe systems (e.g. oil hydraulic servo valve), rolling, pressing, etc. It is important to control the condition of these oils by detecting the solid particles present in the oils and/or examining the viscosities of the oils.

It is also important to detect the particles suspended in the air or examine their concentration in the air in order to monitor the level of air pollution. Such detection includes detection of the particles suspended in the exhaust gas discharged from a plant, a factory or the like.

For such detection of solid particles present in a fluid, a particle sensor comprising a sensor element using a piezoelectric film is disclosed in Japanese Patent Application Laid-open (Kokai) No.7-301594. With this particle sensor, solid particles present in a fluid collide with the detecting section (having a piezoelectric film) of the sensor element or with the vibrating section (mounting the detecting section thereon) of the sensor element; thereby, the vibrating section and the detecting section are vibrated; the piezoelectric film converts the vibration into electric signals; the electric signals are outputted by electrodes holding the piezoelectric film between them.

In detecting solid particles present in a fluid by the use of a particle sensor such as mentioned above, the fluid often contains bubbles besides the solid particles when the fluid is a liquid such as oil or the like. The vibrating section of the particle sensor is vibrated as well by the collision of the bubbles and the signals of this vibration are outputted as well from the detecting section. To accurately know the concentration of solid particles in fluid, it is necessary to distinguish the signals given by the vibration caused by collision of bubbles (the signals are hereinafter referred to as "bubble signals") from the signals given by the vibration caused by collision of solid particles (the signals are hereinafter referred to as "particle signals").

Figure 14:
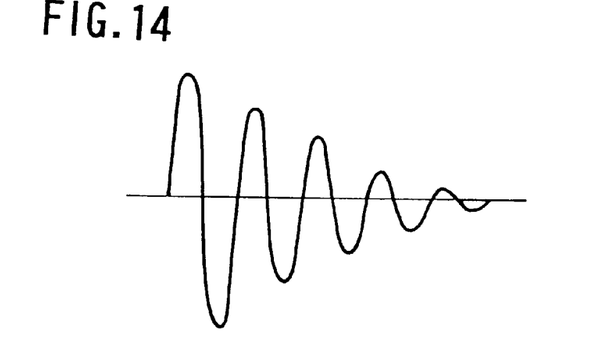
FIG. 14 is a waveform of the signals given by the vibration caused by collision of solid particles (the vibration is the primary resonance vibration of sensor element), obtained with a conventional particle sensor.
Figure 15:
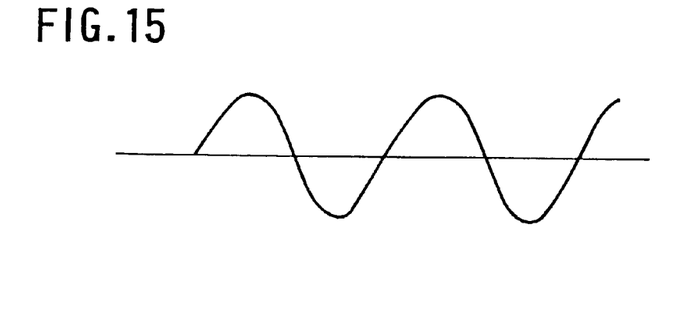
FIG. 15 is a waveform of the signals given by the vibration caused by collision of bubbles (the vibration is a long-period vibration of lower frequency than the primary resonance frequency of sensor element), obtained with a conventional particle sensor.

The vibration of the particle sensor caused by the collision of solid particles generally appears as the primary resonance vibration of the sensor element, such as shown by the signal waveform of FIG. 14. Meanwhile, the vibration of the particle sensor caused by collision of bubbles often appears as a long-period vibration having a frequency lower than the primary resonance frequency of the sensor element, such as shown by the signal waveform of FIG. 15.

Figure 16:
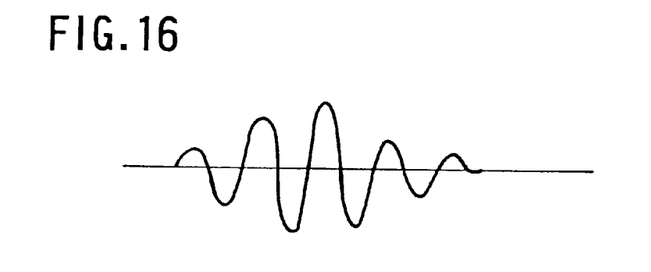
FIG. 16 is a waveform of the signals given by the vibration caused by collision of bubbles (the vibration contains the primary resonance vibration of sensor element), obtained with a conventional particle sensor.
Figure 17:
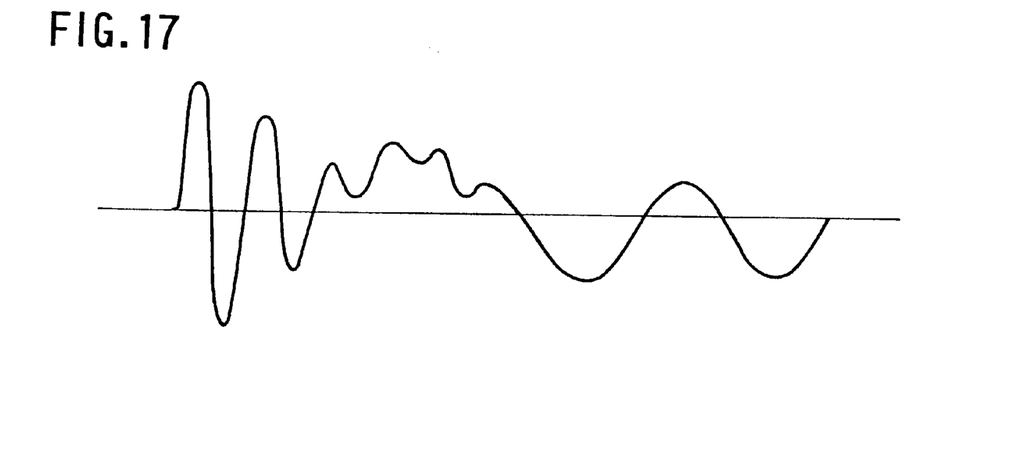
FIG. 17 is a waveform of the signals given by the vibration caused by collision of bubbles (the vibration contains the primary resonance vibration of sensor element), obtained with a conventional particle sensor.

However, collision of bubbles sometimes allows the vibrating section to cause vibrations containing the primary resonance vibration of the sensor element, such as shown by the signal waveform of FIG. 16 or FIG. 17. Such a vibration containing the primary resonance vibration of the sensor element, caused by collision of bubbles is difficult to distinguish from a vibration caused by collision of solid particles; this may result in taking of bubble signals for particle signals when a conventional sensor is used, and has been one reason for the lower accuracy of conventional sensors.

To distinguish the primary resonance vibration caused by collision of bubbles, from the vibration caused by collision of solid particles, there were proposed methods of distinguishing the two vibrations based on the difference in times from starting to reaching maximum amplitude of the primary resonance vibrations of the two collisions, or based on the presence or absence of the vibration components having frequencies lower than the primary resonance frequency, in the primary resonance vibration caused by collision of bubbles. However, none of these methods was sufficient in distinguishability.

SUMMARY OF THE INVENTION

In view of the above situation, the present invention is intended to provide a particle sensor which has improved sensitivity to solid particles and can distinguish particle signals from bubble signals at a high accuracy.

The present inventors made a study in order to clearly distinguish the vibration caused by collision of solid particles, from the vibration caused by collision of bubbles. As a result, the present inventors found out that the vibration caused by collision of solid particles, detected by a particle sensor comprising a fluid flow path and a sensor element, contains, at the initial stage of vibration, vibrational components of higher frequencies than the primary resonance frequency of the sensor element and this phenomenon is unique to the vibration caused by collision of solid particles. The present invention has been completed based on the above finding.

According to the present invention, there is provided a particle sensor comprising:

a flow path of a fluid, having a fluid inlet and a fluid outlet, and a sensor element provided in said flow path, which comprises (a) a vibrating section having such a mass that is sensitive to the collision of solid particles contained in the fluid, with the vibrating section and (b) a detecting section for detecting the vibration of the vibrating section caused by said collision and converting the vibration to electric signals, which sensor has a means capable of selectively detecting any vibration of the vibrating section having a frequency higher than the primary resonance frequency of the sensor element.

Since the particle sensor of the present invention has a means capable of selectively detecting any vibration of higher frequency than the primary resonance frequency of the sensor element of the particle sensor (this vibration is not substantially contained in the vibration caused by collision of bubbles and is contained in the vibration caused by collision of solid particles), the present particle sensor can distinguish particle signals from bubble signals.

DETAILED DESCRIPTION OF THE PREFERED EMBODIMENT

Embodiments of the present invention are described in detail below with reference to the accompanying drawings.

Figure 1:
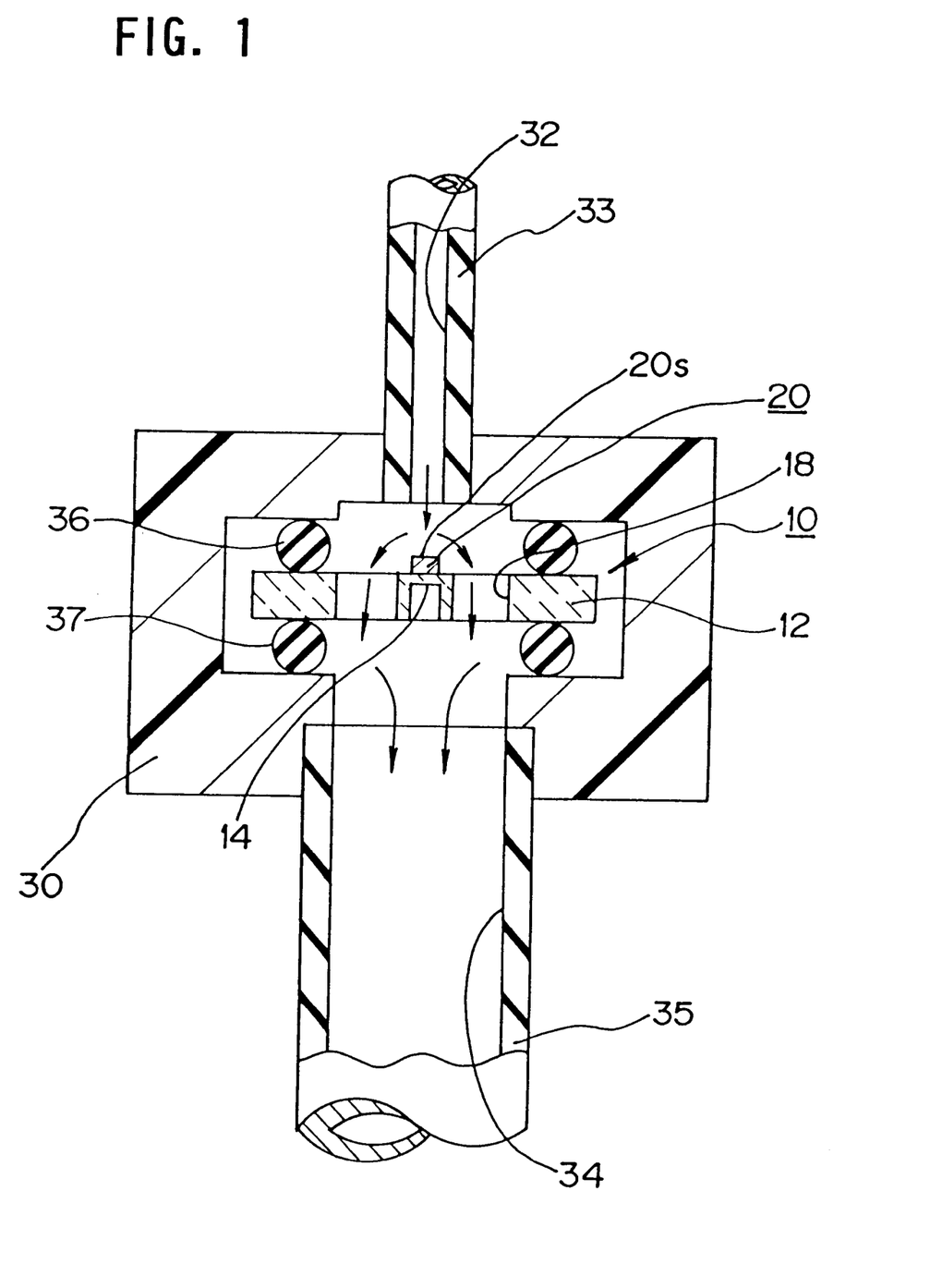
FIG. 1 shows an example of the basic structure of the particle sensor of the present invention.

FIG. 1 shows an example of the basic structure of the particle sensor of the present invention. In this basic structure, the flow path of a fluid is constituted by a nozzle 33 forming the inlet 32 of the fluid, a nozzle 35 forming the outlet of the fluid, and a housing 30 to which the nozzles 33 and 35 are fixed and which accommodates a sensor element 10 between the nozzles 33 and the nozzle 35. The sensor element 10 is fixed to the inside of the housing 30 via elastic members 36 and 37 (e.g. o-rings). The means for fixing the sensor element 10 to the housing inside is not restricted to elastic members and may be screws, adhesives, etc.

In the particle sensor of FIG. 1, the sensor element 10 is provided between the inlet 32 and the outlet 34 of the fluid, the portion of the sensor element 10 in the vicinity of its vibrating section 14 has throughholes 18, and the vibrating section 14 of the sensor element 10 is provided in the flow direction of the fluid determined by the fluid inlet 32 so that the fluid from the inlet 32 can collide with the vibrating section 14, pass through the throughholes 18, and leave the sensor from the fluid outlet 34. The particle sensor having such a structure is called as an axial flow particle sensor and can relatively easily detect vibrations of higher frequencies than the primary resonance frequency of the sensor element of the particle sensor; therefore, the particle sensor is preferably used in the present invention. The particle sensor of the present invention may have other structure.

Figure 2A:
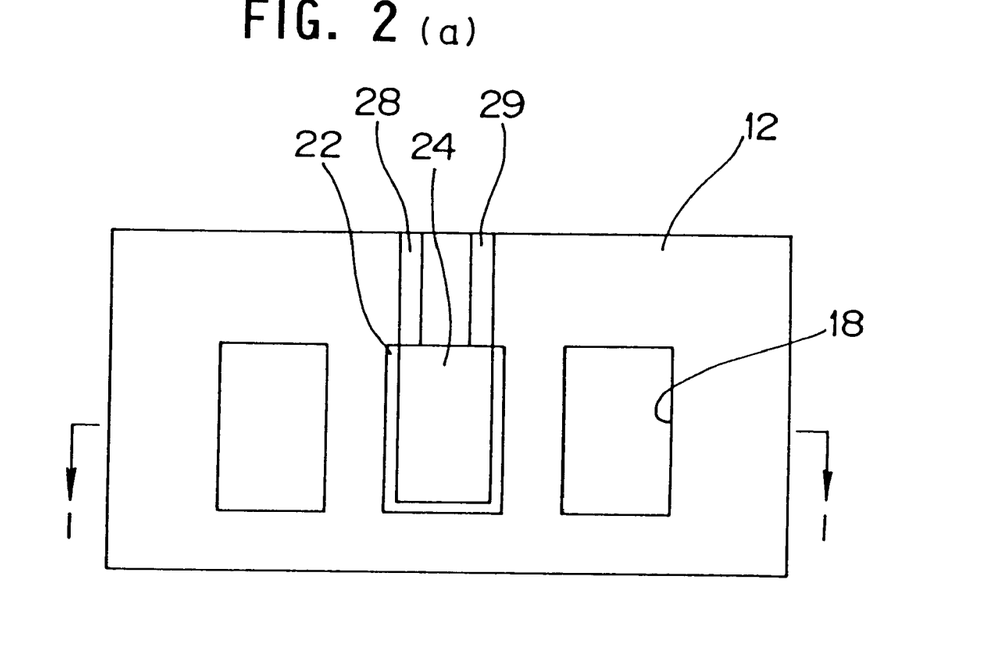
FIG. 2(a) is a plan view showing an example of the sensor element used in the particle sensor of the present invention.
Figure 2B:
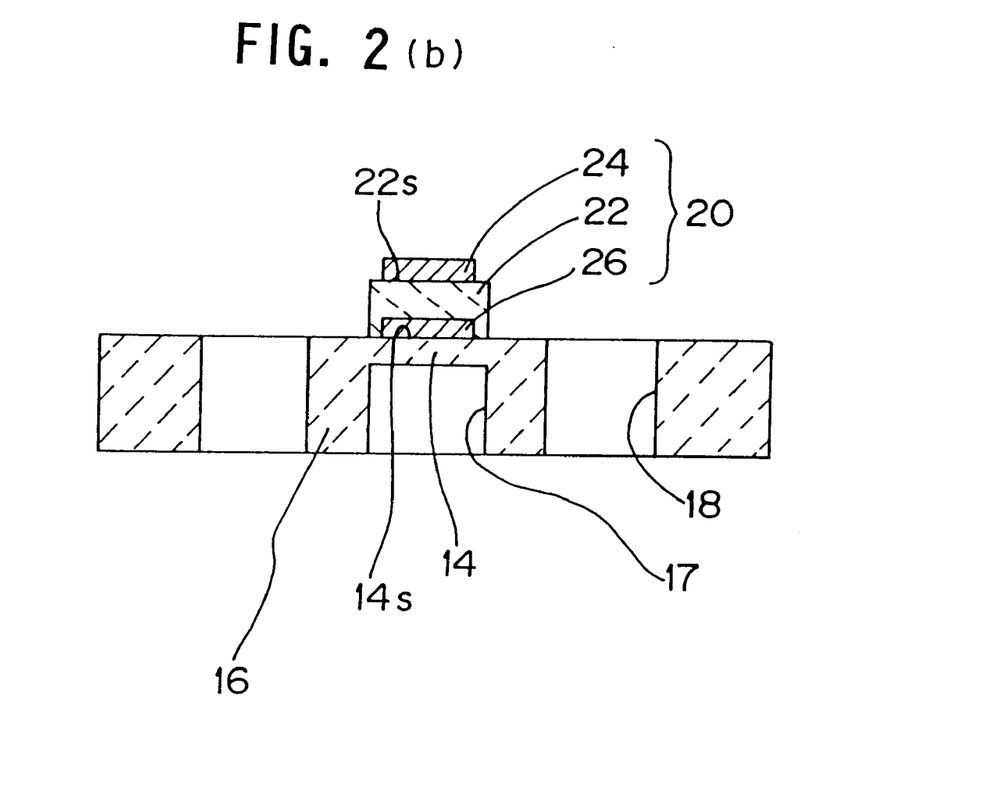
FIG. 2(b) is a sectional view of the sensor element of FIG. 2(a), taken at the I—I line of FIG. 2(a).

FIG. 2(a) is a plan view showing an example of the sensor element used in the particle sensor of the present invention; and FIG. 2(b) is a sectional view of the sensor element of FIG. 2(a), taken at the I—I line of FIG. 2(a). The sensor element comprises a vibrating section 14 having such a mass that is sensitive to the collision of solid particles contained in a fluid, with the vibrating section and a detecting section 20 (a convertor) for detecting the vibration of the vibrating section 14 caused by said collision and converting the vibration to electric signals.

In the present example, the vibrating section 14 is a thin plate and is fixed to a fixing section 16 so that the vibrating section 14 can vibrate, whereby the vibrating section 14 and the fixing section 16 forms a one-piece body 12. A hollow 17 is formed in the body 12 so that the vibrating section 14 can become a thin plate. On one surface 14s of the vibrating section 14 opposite to its surface facing the hollow 17 is provided a detecting section 20. In the portion of the body in the vicinity of the vibrating section 14 are formed a pair of throughholes 18 penetrating the body 12 in the thickness direction.

The vibrating section 14 need not be fixed to the fixing section at the whole periphery as shown in FIG. 2, and may be fixed partially. For example, only one end of the whole periphery of the vibrating section 14 may be fixed to the fixing section 16. The hollow 17 is not restricted to such a hollow as shown in FIG. 2 and may be a closed space. The hollow is formed at the outlet 34 side in the example of FIG. 1 but may be formed at the inlet 32 side. The detecting section 20 is provided at the inlet 32 side relative to the vibrating section 14 in the example of FIG. 1, but may be provided at the outlet 34 side relative to the vibrating section 14.

There is no particular restriction as to the number, shape, etc. of the throughholes 18. However, it is preferable that one pair of the throughholes 18 have the same shape and are provided symmetrically with respect to a virtual plane penetrating the vibrating section 14 in the axial direction. The shape of the body 12 is preferably a plate, but has no particular restriction and can be appropriately determined depending upon the intended application of particle sensor.

The vibrating section 14, when collided by solid particles or bubbles, vibrates, together with the detecting section 20, in a vertical direction, i.e. a direction extending to the detecting section 20 and the hollow 17. In order to detect this vibration advantageously, the vibrating section 14 is preferably a plate. The thickness of the vibrating section 14 is preferably 1–100 $\mu$m. When the thickness is more than 100 $\mu$m, the vibrating section has a low sensitivity to collision; when the thickness is less than 1 $\mu$m, the vibrating section has low mechanical strengths.

The vibrating section 14 is preferably composed of materials which are chemically stable and which undergo no chemical change in contact with various fluids containing solid particles to be detected. The vibrating section 14 is preferably made of a ceramic such as stabilized zirconia, partially stabilized zirconia, magnesia, mullite, aluminum nitride, silicon nitride, glass or the like. The fixing section 16 may be made of the same materials as used in the vibrating section 14, or of different materials.

The detecting section 20 has a piezoelectric film 22, a first electrode 24 and a second electrode 26 with the piezoelectric film being sandwiched between the two electrodes. The first electrode 24 covers at least part of the surface 22s of the piezoelectric film 22, and the second electrode 26 covers at least part of the surface 14s of the vibrating section 14. The piezoelectric film 22 causes, microscopically, dielectric polarization when a stress is applied thereto, and generates, macroscopically, an electric signal (e.g. electric charge or voltage) depending upon the level of the stress. At this time, it is preferable that the piezoelectric film undergoes bending displacement in the thickness direction.

The piezoelectric film 22, when the solid particles and bubbles present in a fluid contact with the first electrode 24 and/or the vibrating section 14, vibrates in its thickness direction together with the vibrating section 14. This vibration applies stress to the piezoelectric film 22, whereby the piezoelectric film 22 generates electric signals. The electric signals are outputted to terminal pads by the first electrode 24 and the second electrode 26 via leads 28 and 29.

The piezoelectric film 22 has a thickness of preferably 1–100 $\mu$m. When the thickness is more than 100 $\mu$m, the film has a low sensitivity; when the thickness is less than 1 $\mu$m, the film has no sufficient reliability.

Preferably, the piezoelectric film is made of a piezoelectric ceramic. It may also be made of an electrostrictive ceramic or a ferroelectric ceramic. Or, it may be made of a material which needs a polarization treatment or no polarization treatment.

The ceramic used in the piezoelectric film includes, for example, a ceramic containing lead zirconate, magnesium lead niobate, nickel lead niobate, zinc lead niobate, manganese lead niobate, antimony lead stannate, lead titanate, manganese lead tungstate, cobalt lead niobate, barium titanate, or any combination thereof. For example, a ceramic composed of magnesium lead niobate, lead zirconate and lead titanate at a ratio close to 20:37:43 has a high Curie point, is superior in piezoelectricity, and is suitable as a material for piezoelectric film. The above ceramic may further contain an appropriate amount of an oxide of lanthanum, calcium, strontium, molybdenum, tungsten, barium, niobium, zinc, nickel, manganese or the like; any combination of said oxides; or other compound. For example, a ceramic composed mainly of magnesium lead niobate, lead zirconate and lead titanate and further containing lanthanum or strontium is preferred.

The first electrode and the second electrode can have appropriate thicknesses depending upon the application of the present particle sensor, but each thicknesses is preferably 0.1–50$\mu$.

The first electrode is preferably composed of an electro-conductive metal which is a solid at room temperature. The metal includes, for example, single metals such as aluminum, titanium, chromium, iron, cobalt, nickel, copper, zinc, niobium, molybdenum, ruthenium, rhodium, silver, tin, tantalum, tungsten, iridium, platinum, gold, lead and the like; and their alloys.

The second electrode is preferably composed of a high-melting metal such as platinum, ruthenium, rhodium, palladium, iridium, titanium, chromium, molybdenum, tantalum, tungsten, nickel, cobalt or the like; or any alloy thereof. It is because the second electrode may be exposed to high temperatures when the piezoelectric film is subjected to a heat treatment and therefore the second electrode is preferably made of a metal resistive to a high-temperature oxidizing atmosphere. The second electrode may be made of a cermet composed of the above-mentioned high-melting metal and a ceramic such as alumina, zirconium oxide, silicon oxide, glass or the like.

In FIG. 1, a fluid enters the housing 30 through the nozzle 33 and contacts with the vibrating section 14 and the detecting section 20 mounted on the vibrating section 14, in such a way that the fluid flow is interrupted by the contact as shown by the arrows. At this time, the solid particles and bubbles present in the fluid collide with the vibrating section 14 and the detecting section 20, whereby the vibrating section 14 and the detecting section 20 vibrate. After contact with the vibrating section 14 and the detecting section 20, the fluid passes through the throughholes 18, passes through the nozzle 35, and leaves the sensor.

Figure 4A:
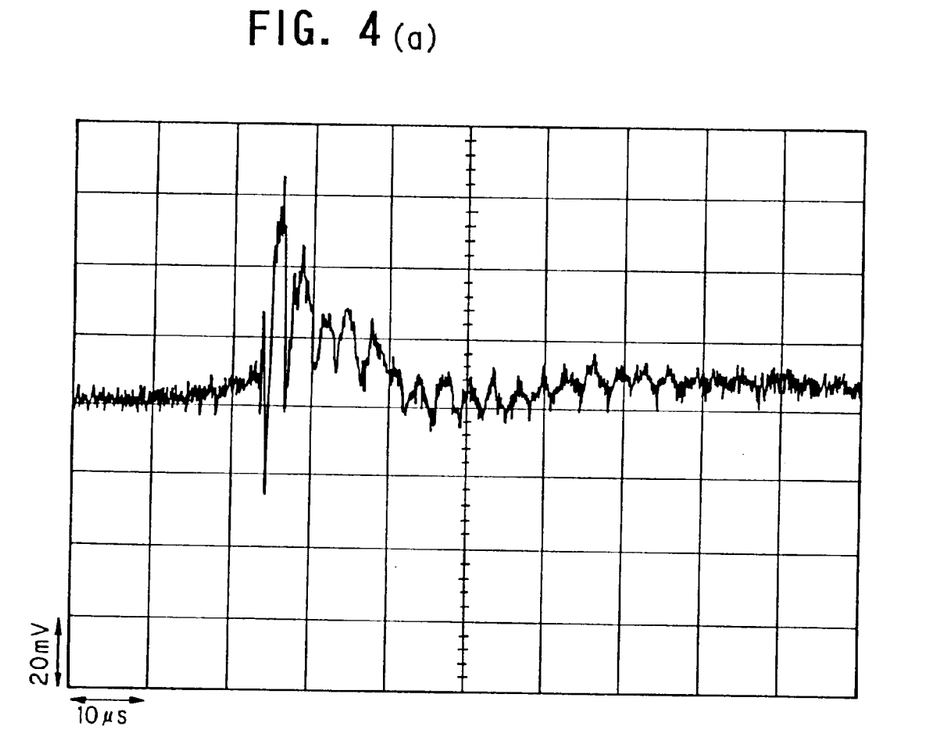
FIG. 4(a) is a waveform of the signals given by the vibration caused by collision of solid particles, obtained with a conventional particle sensor.
Figure 4B:
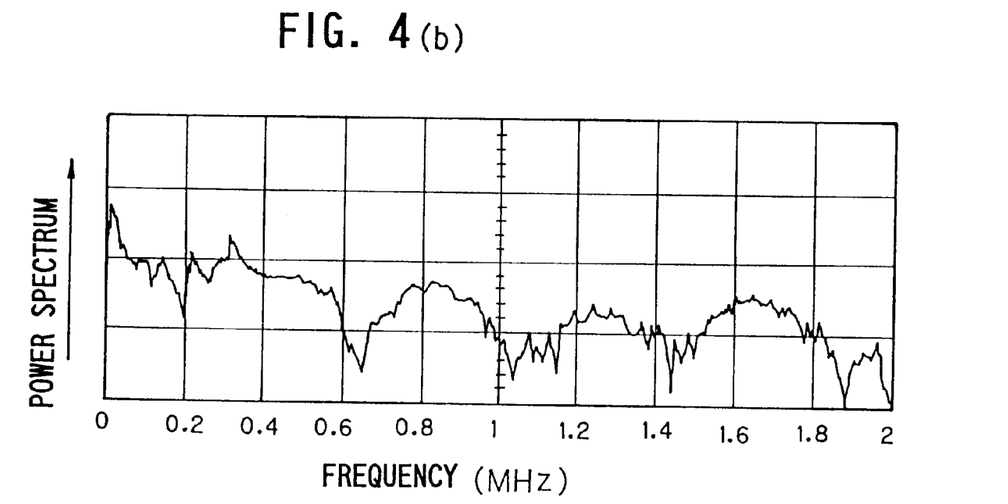
FIG. 4(b) is a graph obtained by subjecting the signals mentioned in FIG. 4(a), to analysis of frequency components.
Figure 5A:
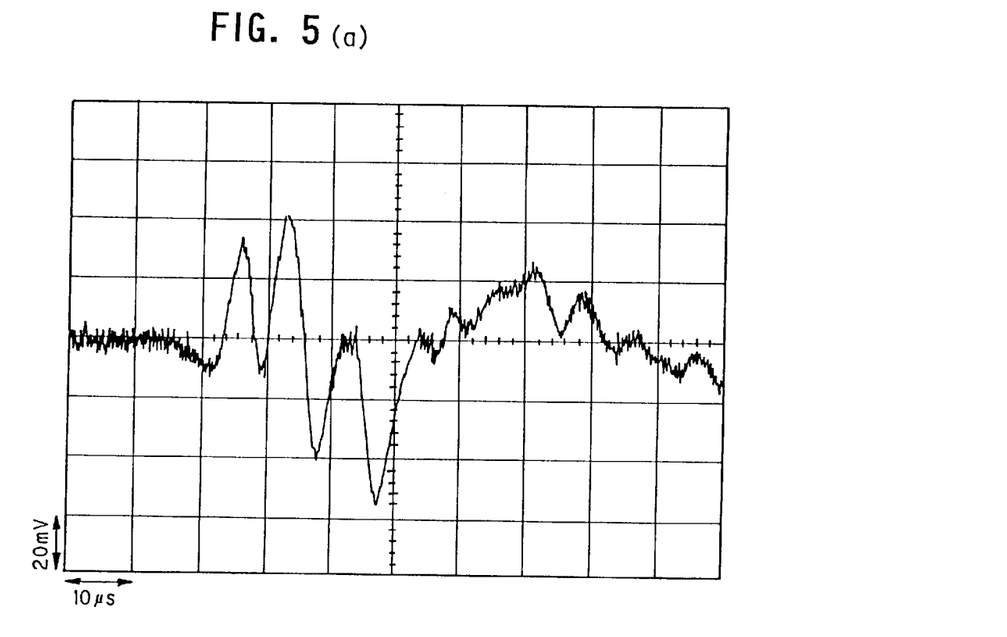
FIG. 5(a) is a waveform of the signals given by the vibration caused by collision of bubbles, obtained with a conventional particle sensor.
Figure 5B:
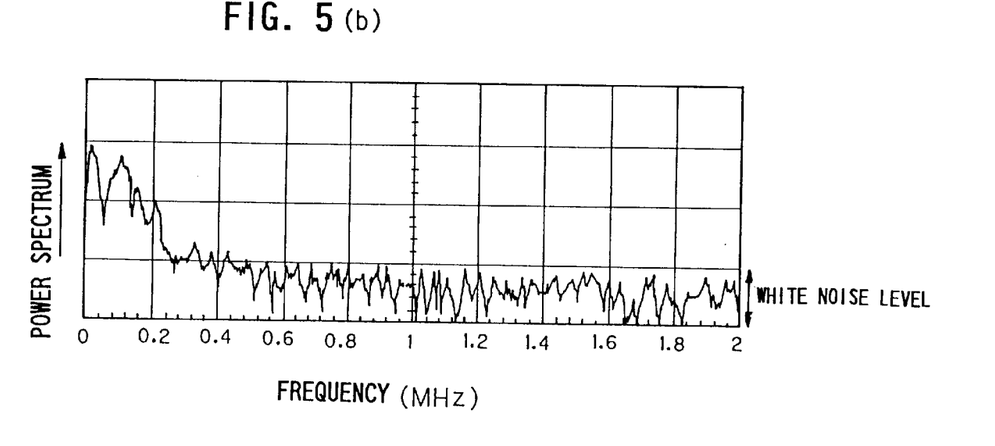
FIG. 5(b) is a graph obtained by subjecting the signals mentioned in FIG. 5(a), to analysis of frequency components.

FIG. 4(a) is a waveform of the particle signals obtained with a particle sensor constructed as in FIG. 1 (the primary resonance frequency of the sensor element is 320 kHz); and FIG. 4(b) is a graph obtained by subjecting the waveform of FIG. 4(a) to analysis of frequency components. FIG. 5(a) is a waveform of the bubble signals obtained with the same sensor; and FIG. 5(b) is a graph obtained by subjecting the waveform of FIG. 5(a) to analysis of frequency components. As is clear from these figures, the waveform of particle signals contains vibrations of higher frequencies than the primary resonance frequency (0.32 MHz) of the sensor element, while the waveform of bubble signals contains substantially no such vibrations.

The particle sensor of the present invention is a particle sensor having a construction as shown in FIG. 1 but further having a means capable of selectively detecting vibrations of higher frequencies than the primary resonance frequency of the sensor element. The means capable of selectively detecting vibrations of higher frequencies than the primary resonance frequency of the sensor element includes, for example, a high-pass filter. By having a high-pass filter capable of selectively detecting vibrations of higher frequencies than the primary resonance frequency of the sensor element, the particle sensor can selectively detect only particle signals by passing the signals outputted from the detecting section, through the high-pass filter.

Figure 6:
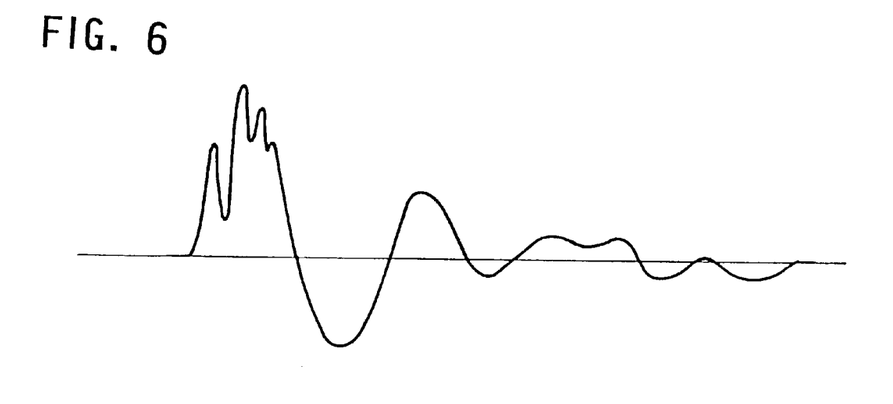
FIG. 6 is a waveform of the signals given by the vibration caused by collision of solid particles, which was obtained with the particle sensor of the present invention having a high-pass filter, before the signals were passed through the high-pass filter.
Figure 7:
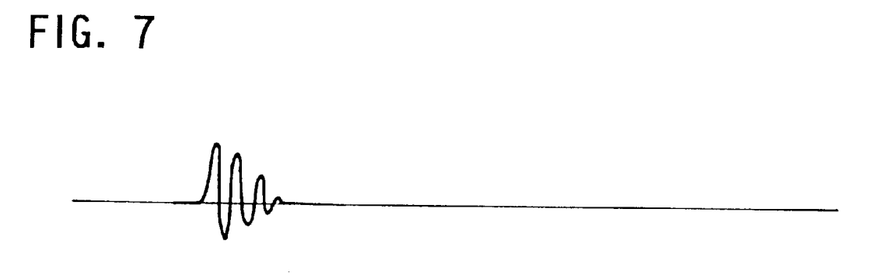
FIG. 7 is a waveform of the signals given by the vibration caused by collision of solid particles, which was obtained with the particle sensor of the present invention having a high-pass filter, after the signals were passed through the high-pass filter.
Figure 8:
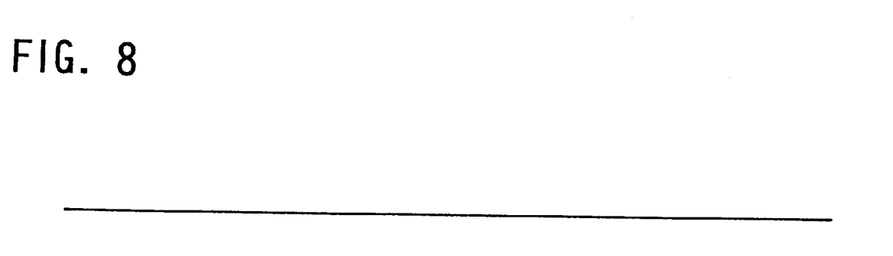
FIG. 8 is a waveform of the signals given by the vibration caused by collision of bubbles, which was obtained with the particle sensor of the present invention having a high-pass filter, after the signals were passed through the high-pass filter.

FIG. 7 is a waveform obtained by passing the particle signals of FIG. 6 through a high-pass filter, wherein only the waveform of vibrations of higher frequencies than the primary resonance frequency of sensor element is shown. FIG. 8 is a waveform obtained by passing bubble signals through a high-pass filter. Since the vibration caused by collision of bubbles contains, in most cases, no vibrations of higher frequencies than the primary resonance frequency of sensor element, capable of passing through the high-pass filter, there appears, in FIG. 8, no waveform as seen in FIG. 7. Thus, by using a high-pass filter, particle signals can be distinguished from bubble signals.

Figure 9:
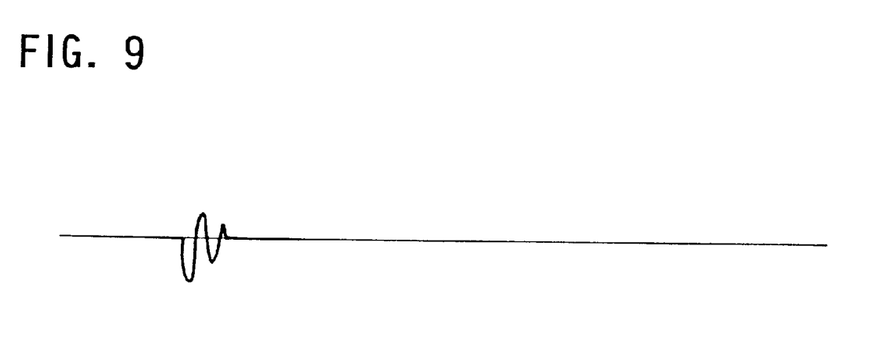
FIG. 9 is a waveform of the signals given by the vibration caused by collision of solid particles, which was obtained with the particle sensor of the present invention having a high-pass filter, after the signals weres passed through the high-pass filter.

When a high-pass filter is used, even if vibrations of higher frequencies than the primary resonance frequency of sensor element appear only rarely (e.g. only 1–2 times) owing to the structure of vibrating section, etc., the signals given by such vibrations can be selectively detected as shown in FIG. 9.

Figure 3:
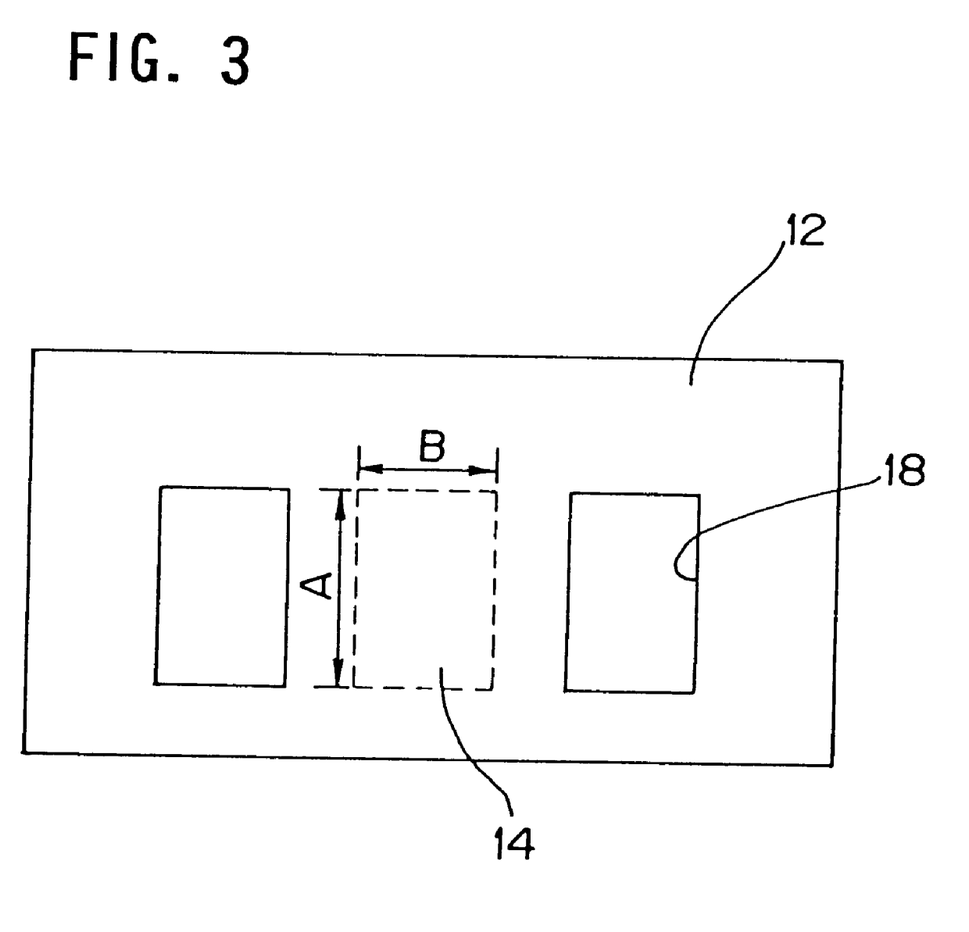
FIG. 3 is a plan view of an example of the sensor element used in the particle sensor of the present invention, wherein the sensor element is illustrated in a state that the detecting section of the sensor element is not mounted on the vibrating section of the sensor element, in order to clearly show the shape of the vibrating section.

The means capable of selectively detecting vibrations of higher frequencies than the primary resonance frequency of sensor element includes a sensor element having a primary resonance frequency of 400 kHz or less, preferably 300 kHz or less. When such a sensor element is used, vibrations of higher frequencies than the primary resonance frequency of sensor element appear easily when solid particles collide with the sensor element. Such a sensor element can be obtained by appropriately selecting or determining the dimension and material of sensor element, the shape of vibrating section, etc. For example, when a sensor element is made so as to have a vibrating section of plate shape of 6 or smaller aspect ratio (that is, in FIG. 3 showing a sensor element mounting no detecting section, the ratio A/B of the long side length A and the short side length B of the vibrating section 14 is made 6 or less), there easily appear vibrations of higher frequencies than the primary resonance frequency of the sensor element.

Figure 10:
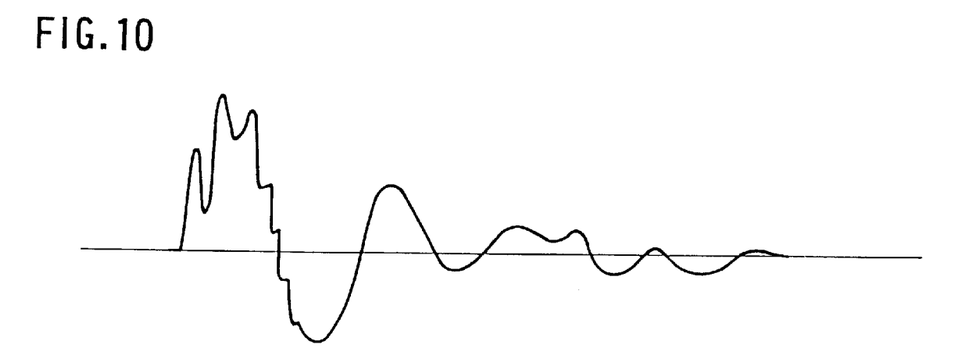
FIG. 10 is a waveform of the signals given by the vibration caused by collision of solid particles, obtained with the particle sensor of the present invention having a sensor element having a primary resonance frequency of 400 kHz or less.
Figure 11:
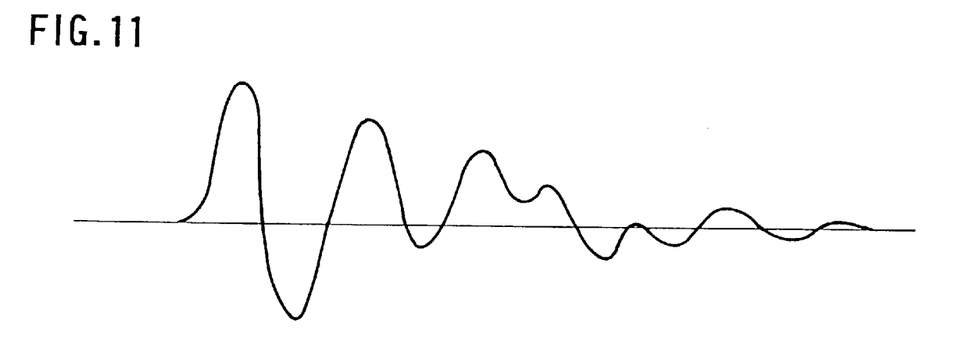
FIG. 11 is a waveform of the signals given by the vibration caused by collision of bubbles, obtained with the particle sensor of the present invention having a sensor element having a primary resonance frequency of 400 kHz or less.
Figure 12:
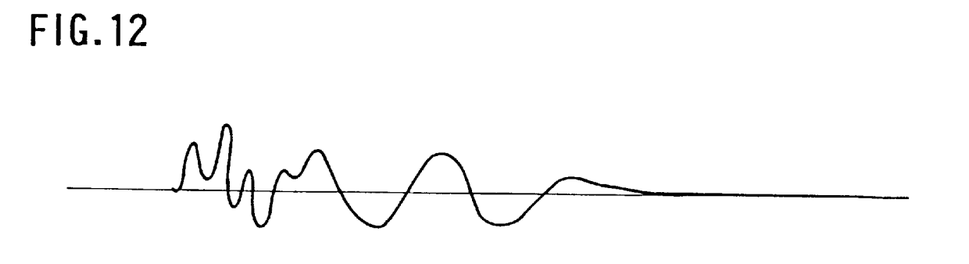
FIG. 12 is a waveform of the signals given by the vibration caused by collision of solid particles, obtained with the particle sensor of the present invention having a sensor element having a primary resonance frequency of 400 kHz or less.
Figure 13:
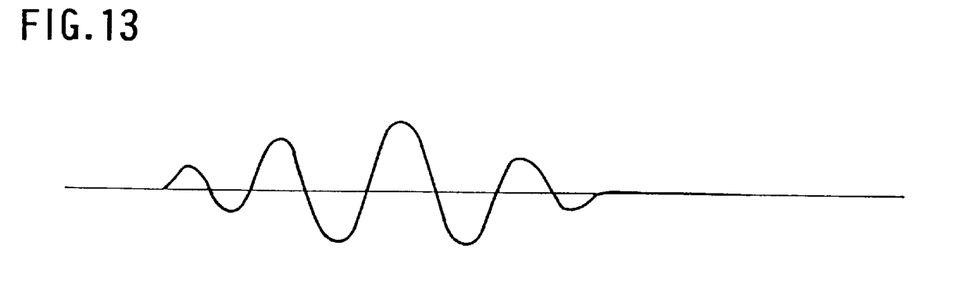
FIG. 13 is a waveform of the signals given by the vibration caused by collision of bubbles, obtained with the particle sensor of the present invention having a sensor element having a primary resonance frequency of 400 kHz or less.

FIG. 10 and FIG. 12 each show a waveform of the particle signals obtained with a particle sensor having the above-mentioned sensor element. FIG. 11 and FIG. 13 each are a waveform of the bubble signals (containing those of the primary resonance vibration of sensor element) obtained with the same particle sensor. Comparison of these figures clearly indicates that FIG. 10 and FIG. 12 each contain, at the start of the vibrations, vibrations of higher frequencies than the primary resonance frequency of sensor element, not present in FIG. 11 and FIG. 13.

As mentioned previously, the present particle sensor, when having a high-pass filter, can detect even vibrations which have higher frequencies than the primary resonance frequency of the sensor element and which appear only rarely. Such vibrations can be detected more clearly by allowing the present particle sensor to have a sensor element having a particular primary resonance frequency such as mentioned above (thereby, vibrations of higher frequencies than the primary resonance frequency of the sensor element appear easily) and further using a high-pass filter.

Bubble signals contain, in some cases, vibrations of higher frequencies than the primary resonance frequency of sensor element. In these cases, the proportion of these bubble signals in total bubble signals is about 10% as shown in Examples described later. Therefore, particle signals can be detected separately from bubble signals, nearly accurately by selectively detecting vibrations of higher frequencies than the primary resonance frequency of sensor element.

As shown in Examples described later, about 10% of bubble signals having higher frequencies than the primary resonance frequency of sensor element, mostly have frequencies of less than two times the primary resonance frequency of sensor element and seldom have frequencies of at least three times the primary resonance frequency of sensor element. Meanwhile, particle signals contain frequencies of at least two times the primary resonance frequency of sensor element and, in almost all cases, contain frequencies of 3–5 times the primary resonance frequency of sensor element.

Therefore, when it is desired to distinguish particles signals from bubble signals at a higher accuracy, it is preferable to selectively detect vibrations of frequencies of at least two times the primary resonance frequency of sensor element. Particle signals can be distinguished more reliably by selectively detecting vibrations of frequencies of at least three times the primary resonance frequency of sensor element.

When particular vibrations are detected selectively, it is preferable to set the frequency upper limit of vibrations to be detected, for the purpose of reducing the high-frequency noise which generates. The frequency upper limit is specifically set at 10 MHz or less, preferably 5 MHz or less, more preferably 2 MHz or less. When the frequency upper limit is set too low, however, the frequency range of signals detected is narrow and the amplitude of signals detected is small. Therefore, the frequency upper limit is determined in view of both the amplitude of signals detected and the high-frequency noise.

Next, description is made on the process for producing the sensor element of the present particle sensor.

The body of the sensor element is made in one piece by laminating a plurality of laminating layers (which are green sheets or green tapes) by hot pressing or the like and then sintering the laminate. For example, in the body 12 of FIG. 2, two laminating layers of green sheets or green tapes are laminated; before the lamination, a throughhole of desired shape to become a hollow 17 is formed in the second layer. Alternatively, the layers may be formed by pressure molding, casting, injection molding or the like and the hollow may be formed by cutting, machining, laser processing, punching by pressing or the like. Although the laminating layers need not have the same thickness, it is preferred that the layers undergo similar shrinkages in sintering.

Formation of a detecting section 20 on the ceramic vibrating section 14 can be conducted as follows. A piezoelectric is formed by pressing using a mold or by tape forming using a material slurry; this piezoelectric before sintering is laminated on the vibrating section of the body before sintering by hot pressing; and sintering is conducted to form a body and a piezoelectric. In this case, electrodes must be formed on the body or the piezoelectric beforehand by a film forming method described later.

Although the sintering temperature for the piezoelectric film is determined appropriately depending upon the materials of the film, the sintering temperature is generally 800–1,400° C., preferably 1,000–1,400° C. In this case, it is preferred for controlling the composition of the piezoelectric film to conduct sintering in the presence of the evaporation source of the components of the piezoelectric film.

In the film forming method, a second electrode 26, a piezoelectric film 22 and a first electrode 24 are laminated in this order on the vibrating section 14 to form a detecting section 20. As the film forming method, there can be appropriately used a known forming method, for example, a thick film method (e.g. screen printing), a coating method (e.g. dipping) or a thin film method [e.g. ion beam, sputtering, vacuum deposition, ion plating, chemical vapor deposition (CVD) or plating]. However, the film forming method is not restricted to these methods. Among these methods, screen printing is preferred because of stable production.

A second electrode 26, leads 28 and 29 and terminal pads can be simultaneously formed by screen printing. A piezoelectric film 22 is preferably formed by screen printing, dipping or the like. In these methods, a piezoelectric film can be formed on the body using a paste or a slurry each containing materials for piezoelectric film and composed mainly of ceramic particles, whereby the piezoelectric film can have good properties.

When a piezoelectric film is formed by a film forming method, since the detecting section and the vibrating section can be bonded integrally without using any adhesive, this method is especially preferred because of the high reliability, reproducibility and integratability. A piezoelectric film may be formed in an appropriate pattern. The pattern may be formed by screen printing, photolithography or the like, or may be formed by removing unnecessary portions using mechanical processing such as laser processing, slicing, ultrasonic processing or the like.

Each film (22, 24 and 26) thus formed on the body may be made integral with the body by heat treatment each time one film is formed, or by heat-treating these films simultaneously after formation of all films. When the first and second electrodes are formed by a thin film method, heat treatment is not always necessary for their integration.

Throughholes 18 may be formed in the green sheets or green tapes or in the laminating layers obtained using a mold, at the time of body formation, by mechanical processing such as cutting, grinding, punching by pressing, or the like. That is, green sheets or the like may be machined so as to form throughholes of desired shape. Throughholes may also be formed by mechanical processing such as laser processing, cutting, ultrasonic processing or the like, after sintering of the body. Throughholes may also be formed after forming a detecting section, using the same processing method.

The detecting section of the present particle sensor was explained in the above, focussing on a device utilizing the piezoelectricity of a piezoelectric film, which device detects the vibration of the vibrating section and converts the vibration into electric signals by piezoelectricity of the film. However, the detecting section is not restricted to the above device utilizing piezoelectricity.

For example, the detecting section may be a device utilizing electromagnetic induction. This device comprises a coil provided on the vibrating section, an electric circuit for detecting electric signals flowing through this coil, and a magnet (which may be an electromagnet) forming a magnetic field in the coil. When the coil vibrates together with the vibrating section, a current flows through the coil owing to electromagnetic induction and is detected by the electric circuit.

The detecting section may be a device utilizing change in static capacity. This device comprises a pair of electrodes provided on the vibrating section, a dielectric held between the electrodes, and an electric circuit connected to the electrodes, and the static capacity stored in this specific space is detected by the electric circuit.

The detecting section may be a device utilizing change in reflected light amount. This device has a means (e.g. a photodiode) for applying a light to the vibrating section and a means for measuring the amount of light reflected by the vibrating section. The means for measuring the amount of light reflected by the vibrating section includes a photosensor. As the vibrating section vibrates, the amount of light reflected by the vibrating section changes, and this change in reflected light amount is measured.

The detecting section may be a device utilizing change in electric resistance caused by the strain of a conductor. This device has a conductor provided on the vibrating section and an electric circuit connected to this conductor. When the conductor vibrates together with the vibrating section, the conductor is strained by the vibration and its resistance changes, and this change in resistance is detected by the electric circuit.

The detecting section may be a device utilizing change in electric resistance caused by the strain of a semiconductor. This device has a semiconductor provided on the vibrating section, and an electric circuit connected to this semiconductor. When the semiconductor vibrates together with the vibrating section, the semiconductor is strained by the vibration and its resistance changes, and this change in resistance is detected by the electric circuit.

The present invention is described in more detail below by way of Examples. However, the present invention is not restricted to these Examples and should be interpreted in a wide range as long as the scope of the present invention is observed.

EXAMPLE 1

There was produced a particle sensor which had a basic structure shown in FIG. 1 and which comprised a sensor element 10 having a primary resonance frequency of 320 kHz. The sensor element comprised a body 12 of 0.3 mm in thickness, made of partially stabilized zirconia. The body 12 comprised a vibrating section 14 having a thickness of 10 $\mu$m and a rectangular shape (shown in FIG. 3) of 2 mm (long side length A) and 0.5 mm (short side length B) (the aspect ratio A/B=4) and made of partially stabilized zirconia. In the body were formed two throughholes 18 of rectangular shape (2 mm×1.5 mm) in the vicinity of the vibrating section 14. The sensor element 10 further comprised, as shown in FIG. 2, a piezoelectric film 22 of 20 $\mu$m in thickness, composed mainly of magnesium lead niobate, lead zirconate and lead titanate and further containing lanthanum and strontium; a first electrode 24 of 0.3 $\mu$m in thickness, made of gold; and a second electrode 26 of 5 $\mu$m in thickness, made of platinum.

Using this particle sensor, there was conducted, as follows, analysis of the frequency components of particle signals and bubble signals. A solid particles-free oil obtained by filtering through a filter paper of about 1 μm filterability and a solid particles-containing oil were each passed through the particle sensor at an oil flow rate of 2.3 liters/min at an oil pressure of 4 kgf/cm$^2$, whereby bubble signals (in the former oil) and particle signals (in the latter oil) were generated. As the solid particles, there were used metal particles of about 1–50 μm in size. Respective signals were amplified by an amplifier, and the amplified signals were passed through a high-pass filter; and the resulting signals were observed using an oscilloscope. The cut-off frequency Fc of the high-pass filter was varied in a certain range and, at each of various cut-off frequencies, the proportion of the number of signals having passed through the high-pass filter, detected by the oscilloscope, to the number of the total signals outputted from the particle sensor was determined. The results are shown in FIG. 18.

Figure 18:
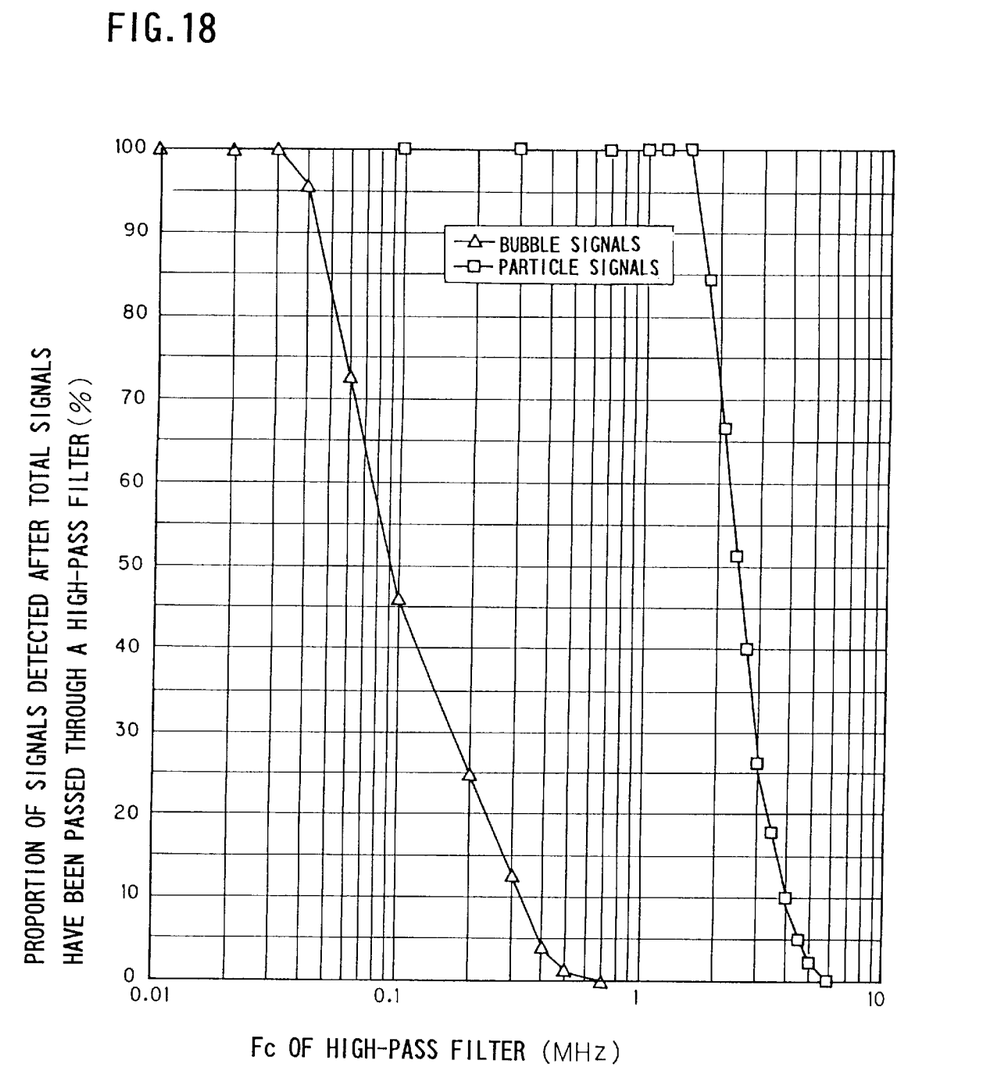
FIG. 18 is a graph showing the results of Example 1.

As is clear from the results of FIG. 18, when the cut-off frequency Fc of the high-pass filter is the same as the primary resonance frequency of the sensor element, i.e. 320 kHz (0.32 MHz), only about 10% of the total bubble signals are detected after the bubble signals have been passed through the high-pass filter. That is, about 90% of the total bubble signals consists of components of frequencies lower than the primary resonance frequency of the sensor element. When the cut-off frequency Fc of the high-pass filter is 700 kHz (0.7 MHz), no bubble signal is detected after the bubble signals have been passed through the high-pass filter. Therefore, even about 10% of the total bubble signals has frequencies lower than 700 kHz, i.e. frequencies less than about two times the primary resonance frequency of the sensor element.

As for the particle signals, total particle signals are detected after having been passed through the high-pass filter, when the cut-off frequency Fc of the high-pass filter is 1.5 MHz; and when the cut-off frequency Fc of the high-pass filter is 1.8 MHz, 84% of the total particle signals is detected after the particle signals have been passed through the high-pass filter. Therefore, all the particle signals have frequencies of 1.5–1.8 MHz (about five times the primary resonance frequency of the sensor element). When the cut-off frequency Fc is 6 MHz, no particle signal is detected after the particle signals have been passed through the high-pass filter. Therefore, even the high-frequency components of the particles signals have frequencies of about 5 MHz.

As is clear from the above, particle signals can be distinguished from bubble signals almost accurately by selectively detecting the vibrations having frequencies higher than the primary resonance frequency of sensor element. Since about 10% of the total bubble signals has frequencies ranging from the primary resonance frequency of sensor element to less than two times the primary resonance frequency of sensor element, particle signals and such bubble signals (about 10%) can be distinguished from each other by selectively detecting the vibrations having frequencies of at least two times the primary resonance frequency of sensor element. Particle signals and bubble signals can be more accurately distinguished from each other by selectively detecting the vibrations having frequencies of at least three times the primary resonance frequency of sensor element. In selective detection of particle signals, it is preferred to set the upper limit of frequencies to be detected, for the purpose of reducing high-frequency noise. The upper limit can be set at about 10 MHz in view of the frequency components of particle signals, etc.

EXAMPLE 2

Analysis of the frequency components of particle signals and bubble signals was conducted in the same manner as in Example 1 except that the oil flow rate was 1.6 liters/min, 2.3 liters/min or 3.2 liters/min. The results are shown in FIG. 19.

EXAMPLE 3

Analysis of the frequency components of particle signals and bubble signals was conducted in the same manner as in Example 1 except that the oil pressure was 2.4 kgf/cm$^2$, 4 kgf/cm$^2$ or 6 kgf/cm$^2$. The results are shown in FIG. 20.

Figure 19:
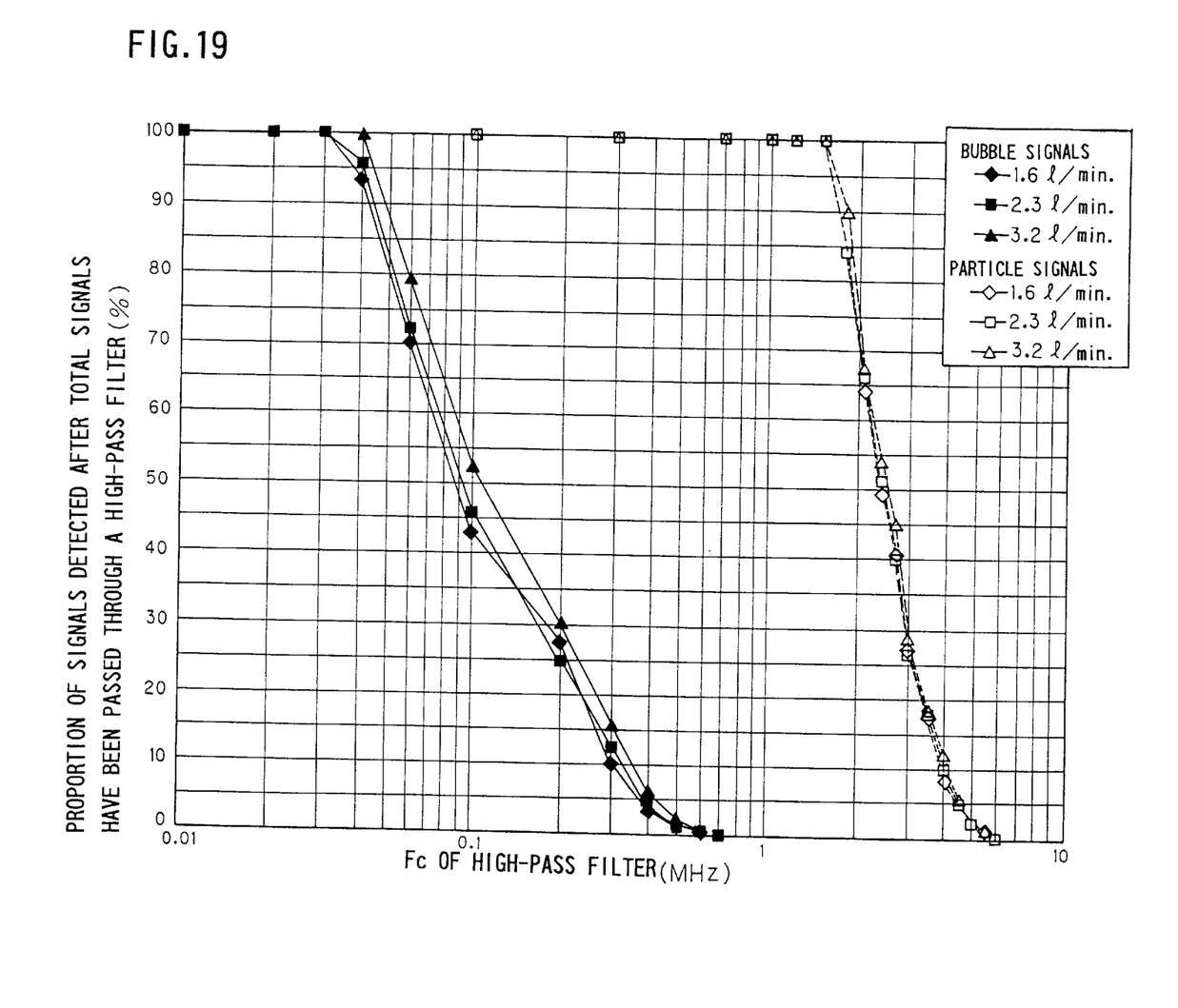
FIG. 19 is a graph showing the results of Example 2.
Figure 20:
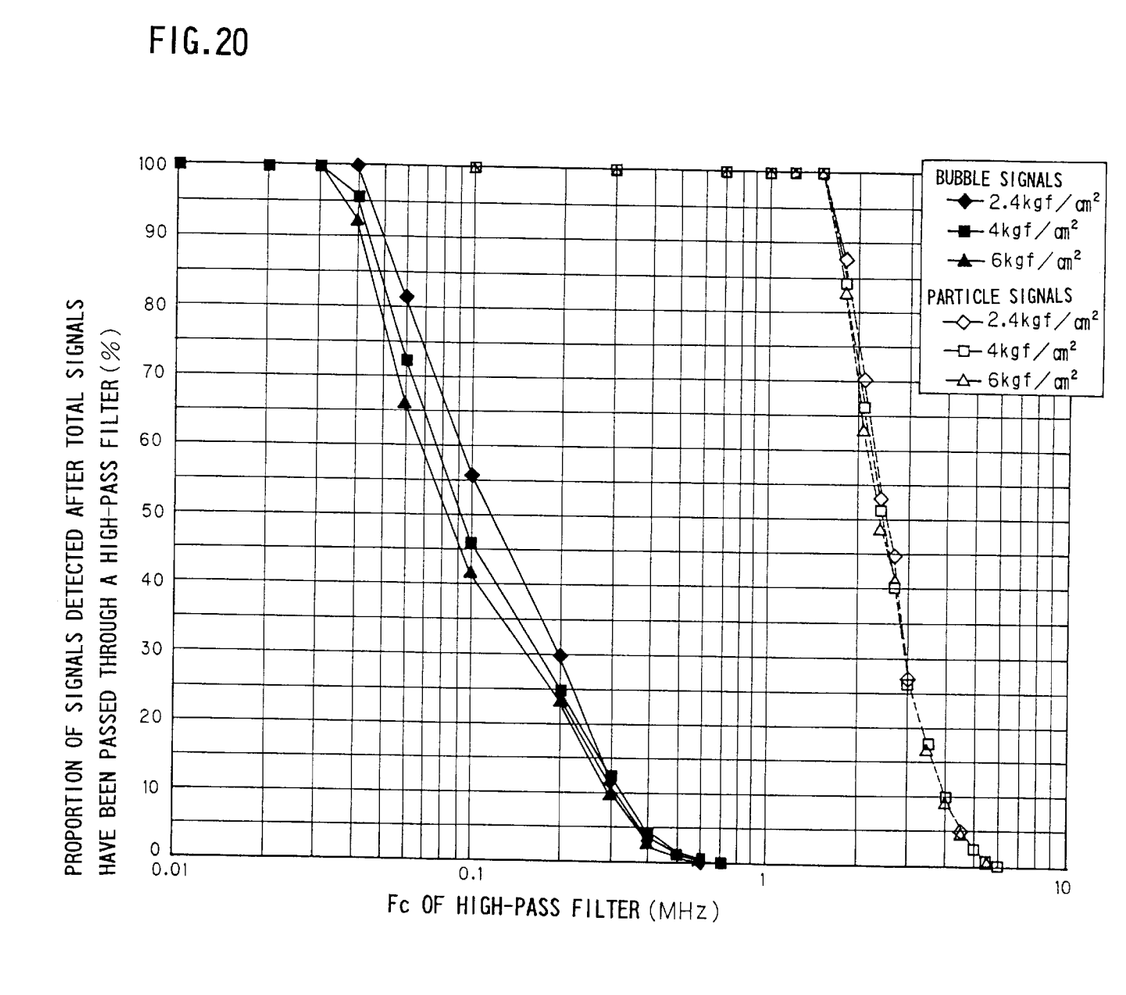
FIG. 20 is a graph showing the results of Example 3.

As is clear from the results of FIG. 19 and FIG. 20, the proportion of the signals passing through the high-pass filter shows substantially no change even when the rate or pressure of the oil passing through the sensor element is changed.

EXAMPLE 4

Analysis of the frequency components of particle signals and bubble signals was conducted in the same manner as in Example 1 except that there was used a particle sensor comprising a sensor element 10 which had a rectangular vibrating section 14 of 2 mm (long side length A) and 0.3 mm (short side length B) (the aspect ratio A/B=6.7) and which had a primary resonance frequency of 610 kHz. The results are shown in FIG. 21.

Figure 21:
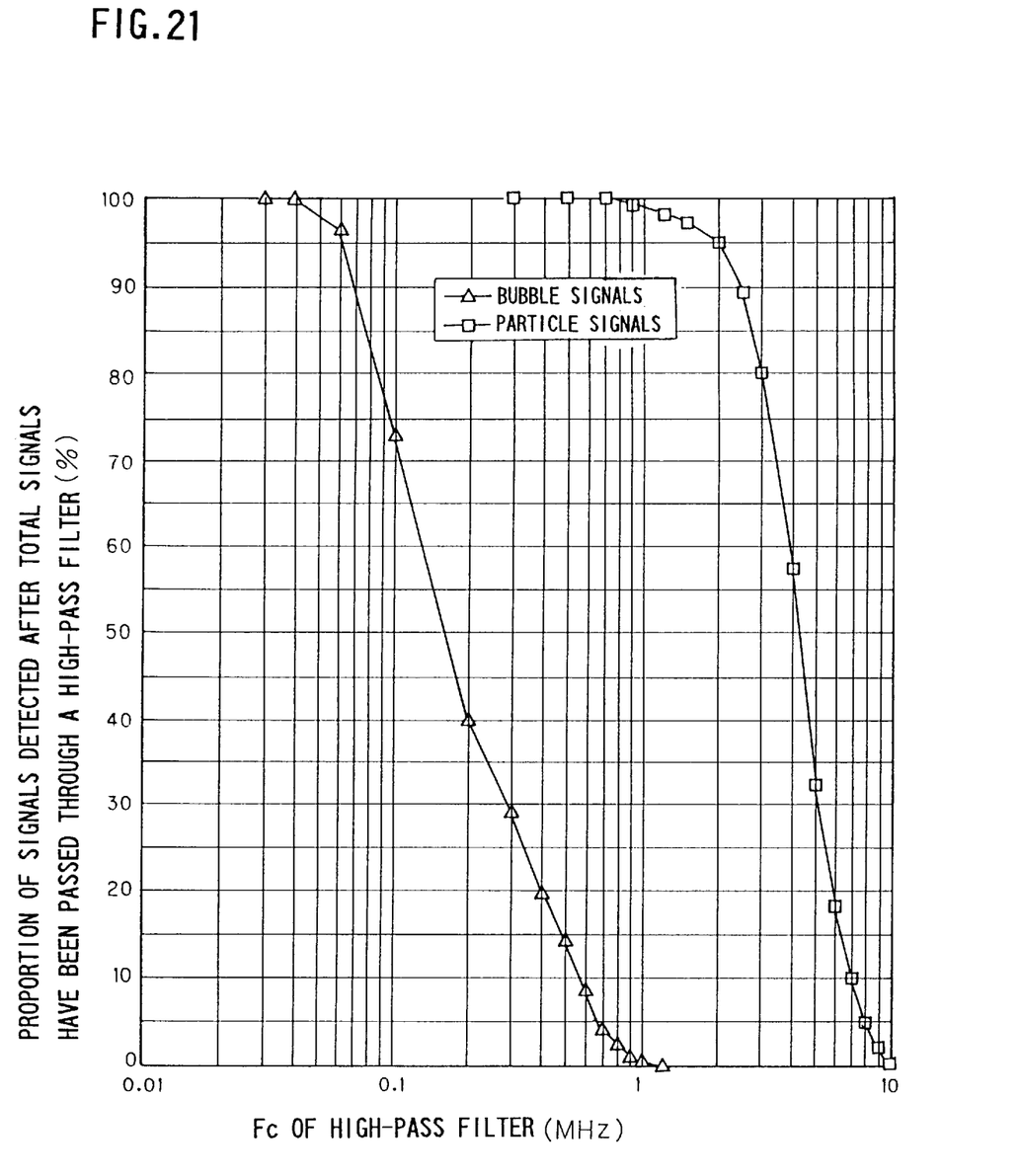
FIG. 21 is a graph showing the results of Example 4.

As is clear from the results of FIG. 21, when the cut-off frequency Fc of the high-pass filter is the same as the primary resonance frequency of the sensor element, i.e. 610 kHz (0.61 MHz), only about 8% of the total bubble signals is detected after the bubble signals have been passed through the high-pass filter. That is, about 92% of the total bubble signals consists of components of frequencies lower than the primary resonance frequency of the sensor element. When the cut-off frequency Fc of the high-pass filter is 1.2 MHz, no bubble signal is detected after the bubble signals have been passed through the high-pass filter. Therefore, even about 8% of the bubbles signals has frequencies lower than 1.2 MHz, i.e. frequencies lower than about two times the primary resonance frequency of the sensor element.

As for the particle signals, all the particle signals are detected after having been passed through the high-pass filter, when the cut-off frequency Fc of the high-pass filter is 0.7 MHz; and when the cut-off frequency Fc of the high-pass filter is 10 MHz, no particle signal is detected after the particle signals have been passed through the high-pass filter.

As is appreciated from the above, even when the shape of sensor element is changed or the primary resonance frequency of sensor element is changed, about 90% of the total bubble signals has frequencies lower than the primary resonance frequency of sensor element, and remaining about 10% of the bubble signals has frequencies lower than two times the primary resonance frequency of sensor element. The cut-off frequency Fc at which the proportion of the particle signals detected after having been passed through the high-pass filter becomes 100%, is lower in Example 4 than in Example 1. This is due to the difference in the aspect ratio of vibrating section of sensor element. A smaller aspect ratio of vibrating section tends to give vibrations of higher frequencies than the primary resonance frequency of sensor element.

Incidentally, also when there were used, as the solid particles, particles of 50 μm or more in size or particles of other material (e.g. ceramic), particle signals having frequency characteristics similar to the above were obtained.

As described above, the particle sensor of the present invention can selectively detect vibrations having frequencies higher than the primary resonance frequency of the sensor element, which vibrations appear mainly when solid particles collide with the sensor element; therefore, the particle sensor can distinguish particle signals from bubble signals at a higher accuracy. Further, because of this distinguishability, the present particle sensor has improved sensitivity to solid particles by removing bubble signals.

What is claimed is:

1. A particle sensor for sensing solid particles contained in a liquid comprising:

a flow path for a liquid having a liquid inlet and a liquid outlet, and a sensor element provided in said flow path, which comprises (a) a vibrating section having a vibratable element of a mass such that it is sensitive to the collision of said solid particles contained in a liquid with the vibratable element and (b) a detecting section for detecting the vibration of the vibrating element caused by said collision and converting the vibration to electric output signals, said vibratable element having a vibrational mode having a primary resonant frequency, said detecting section having means for discriminating in said electrical output signals between signals indicative of collision of a solid particle from signals indicative of collision of a bubble with said vibratable element, and means arranged to selectively detect vibrations of said vibratable element in said vibrational mode having frequencies which are higher than said primary resonance frequency, said selectively detected vibrations of higher frequencies being indicative of particle collision.

2. A particle sensor according to claim 1, wherein a portion of the sensor element in the vicinity of the vibratable element has throughholes, and the vibratable element is provided in the flow direction of a liquid determined by the liquid inlet so that the liquid from the liquid inlet collides with the vibratable element, passes through the throughholes, and leaves the sensor from the liquid outlet.

3. A particle sensor according to claim 1, wherein said means arranged to selectively detect vibrations of the vibratable element is a high-pass filter.

4. A particle sensor according to claim 1, wherein said primary resonance frequency of the sensor element is 400 kHz or less.

5. A particle sensor according to claim 1, wherein the means arranged to selectively detect vibrations of the vibratable element selects vibrations of the vibratable element having a frequency of at least two times the primary resonance frequency of the sensor element.

6. A particle sensor according to claim 1, wherein the means arranged to selectively detect vibrations of the vibratable element selects vibrations of the vibratable element having a frequency of at least three times the primary resonance frequency of the sensor element.

7. A particle sensor according to claim 1, wherein the means arranged to selectively detect vibrations of the vibratable element selects vibrations of the vibrating section having a frequency of 10 MHz or less.

8. A particle sensor according to claim 1, wherein the means arranged to selectively detect vibrations of the vibratable element selects vibrations of the vibratable element having a frequency of 5 MHz or less.

9. A particle sensor according to claim 1, wherein the means arranged to selectively detect vibrations of the vibratable element selects vibrations of the vibratable element having a frequency of 2 MHz or less.

* * * * *